(12) United States Patent
Gowans et al.

(10) Patent No.: US 11,116,669 B2
(45) Date of Patent: Sep. 14, 2021

(54) ABSORBENT NEGATIVE PRESSURE WOUND THERAPY DRESSING

(71) Applicant: Smith & Nephew PLC, Watford (GB)

(72) Inventors: John Philip Gowans, Hessle (GB); William Kelbie, Inverness (GB); Stephanie Jane Noble, Hull (GB)

(73) Assignee: Smith & Nephew PLC, Watford (GB)

( * ) Notice: Subject to any disclaimer, the term of this patent is extended or adjusted under 35 U.S.C. 154(b) by 317 days.

(21) Appl. No.: 16/328,180

(22) PCT Filed: Aug. 24, 2017

(86) PCT No.: PCT/EP2017/071322
§ 371 (c)(1),
(2) Date: Feb. 25, 2019

(87) PCT Pub. No.: WO2018/037075
PCT Pub. Date: Mar. 1, 2018

(65) Prior Publication Data
US 2019/0192350 A1 Jun. 27, 2019

Related U.S. Application Data

(60) Provisional application No. 62/379,667, filed on Aug. 25, 2016.

(51) Int. Cl.
*A61F 13/00* (2006.01)
*A61F 13/02* (2006.01)
*A61M 1/00* (2006.01)

(52) U.S. Cl.
CPC .... *A61F 13/00068* (2013.01); *A61F 13/0216* (2013.01); *A61M 1/90* (2021.05); *A61M 1/962* (2021.05); *A61M 1/86* (2021.05)

(58) Field of Classification Search
CPC .......... A61F 13/00068; A61F 13/0216; A61F 13/0206; A61M 1/009; A61M 1/90; A61M 1/962; A61M 1/0088; A61M 1/0086
(Continued)

(56) References Cited

U.S. PATENT DOCUMENTS 3,874,387 A 4/1975 Barbieri
4,224,941 A 9/1980 Stivala
(Continued)

FOREIGN PATENT DOCUMENTS

CN 201664463 U 12/2010
DE 198 44 355 4/2000
(Continued)

OTHER PUBLICATIONS

"Electronics Overmolding: Silicone Overmolding: Konarksilicones." Konark Silicone Technologies, www.konarksilicones.com/electronics-silicone-overmolding/. (Year: 2015).*
(Continued)

*Primary Examiner* — Nicholas J Weiss
*Assistant Examiner* — Seth Han
(74) *Attorney, Agent, or Firm* — Knobbe, Martens, Olson & Bear, LLP

(57) ABSTRACT

Disclosed herein are embodiments of a wound treatment apparatus employing hydrophobic and hydrophilic dressing materials and/or coating of the layers of a wound dressing. In some embodiments, the hydrophobic and hydrophilic dressing materials and/or coating controls the migration of fluid within the wound dressing.

10 Claims, 11 Drawing Sheets

(58) Field of Classification Search
USPC ........................................................ 604/319
See application file for complete search history.

(56) References Cited

U.S. PATENT DOCUMENTS

| | | | |
|---|---|---|---|
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,216,651 B2 | 5/2007 | Argenta et al. |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,699,823 B2 | 4/2010 | Haggstrom et al. |
| 7,776,028 B2 | 8/2010 | Miller et al. |
| 7,779,625 B2 | 8/2010 | Joshi et al. |
| D625,422 S | 10/2010 | Arbesman et al. |
| 7,837,673 B2 | 11/2010 | Vogel |
| 7,838,717 B2 | 11/2010 | Haggstrom et al. |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,062,273 B2 | 11/2011 | Weston |
| 8,080,702 B2 | 12/2011 | Blott et al. |
| 8,092,441 B2 | 1/2012 | Sugito |
| 8,118,794 B2 | 2/2012 | Weston et al. |
| 8,158,844 B2 | 4/2012 | McNeil |
| 8,167,869 B2 | 5/2012 | Wudyka |
| 8,207,392 B2 | 6/2012 | Haggstrom et al. |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,372,049 B2 | 2/2013 | Jaeb et al. |
| 8,372,050 B2 | 2/2013 | Jaeb et al. |
| 8,404,921 B2 | 3/2013 | Lee et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,444,612 B2 | 5/2013 | Patel et al. |
| 8,449,508 B2 | 5/2013 | Coulthard et al. |
| 8,460,255 B2 | 6/2013 | Joshi et al. |
| 8,500,776 B2 | 8/2013 | Ebner |
| 8,529,548 B2 | 9/2013 | Blott et al. |
| 8,545,464 B2 | 10/2013 | Weston |
| 8,545,466 B2 | 10/2013 | Andresen et al. |
| 8,569,566 B2 | 10/2013 | Blott et al. |
| 8,579,872 B2 | 11/2013 | Coulthard et al. |
| 8,603,074 B2 | 12/2013 | Kagan |
| 8,604,265 B2 | 12/2013 | Locke et al. |
| 8,628,505 B2 | 1/2014 | Weston |
| 8,641,691 B2 | 2/2014 | Fink |
| 8,641,693 B2 | 2/2014 | Locke et al. |
| 8,702,665 B2 | 4/2014 | Locke et al. |
| 8,764,732 B2 | 7/2014 | Hartwell |
| 8,795,257 B2 | 8/2014 | Coulthard et al. |
| 8,808,274 B2 | 8/2014 | Hartwell |
| 8,814,842 B2 | 8/2014 | Coulthard et al. |
| 8,821,458 B2 | 9/2014 | Locke et al. |
| 8,829,263 B2 | 9/2014 | Haggstrom et al. |
| 8,870,837 B2 | 10/2014 | Locke et al. |
| 8,915,895 B2 | 12/2014 | Jaeb et al. |
| 8,961,496 B2 | 2/2015 | Locke et al. |
| 8,974,429 B2 | 3/2015 | Gordon et al. |
| 9,050,209 B2 | 6/2015 | Coulthard et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,168,330 B2 | 10/2015 | Joshi et al. |
| 9,198,802 B2 | 12/2015 | Robinson et al. |
| 9,220,822 B2 | 12/2015 | Hartwell et al. |
| 9,259,558 B2 | 2/2016 | Tsai |
| 9,265,665 B2 | 2/2016 | Robinson et al. |
| 9,265,867 B2 | 2/2016 | Coulthard et al. |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,452,088 B2 | 9/2016 | Shulman et al. |
| 9,452,245 B2 | 9/2016 | Jaeb et al. |
| 9,560,975 B2 | 2/2017 | Mei et al. |
| 9,629,986 B2 | 4/2017 | Patel et al. |
| D787,690 S | 5/2017 | Mackay et al. |
| 9,669,138 B2 | 6/2017 | Joshi et al. |
| 9,737,649 B2 | 8/2017 | Begin et al. |
| 9,770,368 B2 | 9/2017 | Robinson et al. |
| 9,795,725 B2 | 10/2017 | Joshi et al. |
| 9,814,811 B2 | 11/2017 | Aalders et al. |
| 9,844,475 B2 | 12/2017 | Hartwell |
| 9,925,092 B2 | 3/2018 | Luckemeyer et al. |
| RE46,778 E | 4/2018 | Peron |
| 9,956,120 B2 | 5/2018 | Locke |
| 10,004,914 B2 | 6/2018 | Nettesheim et al. |

(56) References Cited

U.S. PATENT DOCUMENTS

| | | |
|---|---|---|
| 10,016,544 B2 | 7/2018 | Coulthard et al. |
| 10,086,117 B2 | 10/2018 | Locke et al. |
| 10,123,909 B2 | 11/2018 | Hartwell |
| 2003/0212357 A1 | 11/2003 | Pace |
| 2004/0064132 A1 | 4/2004 | Boehringer et al. |
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1 | 3/2005 | Sweetland et al. |
| 2005/0065471 A1 | 3/2005 | Kuntz |
| 2005/0119737 A1 | 6/2005 | Bene et al. |
| 2005/0131327 A1 | 6/2005 | Lockwood et al. |
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0213527 A1 | 9/2006 | Argenta et al. |
| 2006/0259102 A1 | 11/2006 | Slatkine |
| 2007/0055209 A1 | 3/2007 | Patel et al. |
| 2007/0078366 A1* | 4/2007 | Haggstrom ....... A61F 13/00063 602/53 |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2008/0021356 A1 | 1/2008 | Castello Escude et al. |
| 2008/0051716 A1 | 2/2008 | Stutz |
| 2009/0012484 A1 | 1/2009 | Nielsen et al. |
| 2009/0048556 A1 | 2/2009 | Durand |
| 2010/0022990 A1 | 1/2010 | Karpowicz et al. |
| 2010/0100160 A1 | 4/2010 | Edman et al. |
| 2010/0137775 A1 | 6/2010 | Hu et al. |
| 2010/0160881 A1 | 6/2010 | Lin et al. |
| 2010/0280469 A1 | 11/2010 | Hall |
| 2010/0292632 A1 | 11/2010 | Mulvihill et al. |
| 2011/0112492 A1 | 5/2011 | Bharti et al. |
| 2011/0224631 A1 | 9/2011 | Simmons |
| 2011/0292623 A1 | 12/2011 | Stanley |
| 2011/0305736 A1 | 12/2011 | Wieland et al. |
| 2012/0059294 A1 | 3/2012 | Schubert et al. |
| 2012/0109034 A1 | 5/2012 | Locke et al. |
| 2012/0253302 A1 | 10/2012 | Corley |
| 2013/0090615 A1 | 4/2013 | Jaeb et al. |
| 2013/0102979 A1 | 4/2013 | Coulthard et al. |
| 2013/0215638 A1 | 8/2013 | Dabov et al. |
| 2014/0100536 A1 | 4/2014 | Angel |
| 2014/0330227 A1 | 11/2014 | Coulthard et al. |
| 2014/0343518 A1 | 11/2014 | Riesinger |
| 2015/0057625 A1* | 2/2015 | Coulthard .......... A61F 13/0216 604/319 |
| 2015/0065965 A1 | 3/2015 | Haggstrom et al. |
| 2015/0174304 A1* | 6/2015 | Askem ................ A61M 1/0027 604/319 |
| 2015/0202354 A1 | 7/2015 | Wall |
| 2015/0258256 A1 | 9/2015 | Jaeb et al. |
| 2015/0250931 A1 | 10/2015 | Bharti et al. |
| 2016/0015873 A1 | 1/2016 | Robinson et al. |
| 2016/0058927 A1 | 3/2016 | Weston |
| 2016/0081859 A1 | 3/2016 | Hartwell |
| 2016/0120706 A1 | 5/2016 | Collinson et al. |
| 2016/0166438 A1 | 6/2016 | Rovaniemi |
| 2016/0199546 A1 | 7/2016 | Chao |
| 2016/0206793 A1 | 7/2016 | Robinson et al. |
| 2016/0242964 A1 | 8/2016 | Rapp et al. |
| 2016/0271305 A1 | 9/2016 | Kurihara et al. |
| 2016/0361473 A1 | 12/2016 | Robinson et al. |
| 2017/0112974 A1 | 4/2017 | Fujisaki |
| 2017/0112975 A1 | 4/2017 | Fujisaki |
| 2017/0127525 A1 | 5/2017 | Schonholz |
| 2017/0232189 A1 | 8/2017 | Qin et al. |
| 2017/0296714 A1 | 10/2017 | Locke et al. |
| 2017/0304510 A1 | 10/2017 | Askem et al. |
| 2017/0319761 A1 | 11/2017 | Locke et al. |
| 2017/0326277 A1 | 11/2017 | Huang |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0104393 A1 | 4/2018 | Wu et al. |
| 2018/0200414 A1 | 7/2018 | Askem et al. |
| 2018/0296397 A1 | 10/2018 | Askem et al. |
| 2018/0311078 A1 | 11/2018 | Hartwell |
| 2018/0318137 A1 | 11/2018 | Donda et al. |
| 2018/0318165 A1 | 11/2018 | Donda et al. |
| 2018/0353771 A1 | 12/2018 | Kim et al. |
| 2019/0021911 A1 | 1/2019 | Askem et al. |
| 2019/0125943 A1 | 5/2019 | Askem et al. |
| 2019/0143007 A1 | 5/2019 | Askem et al. |
| 2019/0282737 A1 | 9/2019 | Beadle et al. |
| 2020/0022846 A1 | 1/2020 | Beadle et al. |

FOREIGN PATENT DOCUMENTS

| | | |
|---|---|---|
| EP | 0 512 543 | 11/1992 |
| EP | 1411874 A1 | 4/2004 |
| EP | 1455701 B1 | 3/2006 |
| EP | 1807032 A1 | 7/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 2659915 A1 | 11/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2 345 437 | 4/2014 |
| EP | 2305325 B1 | 4/2014 |
| EP | 2323712 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |
| EP | 2268348 B1 | 12/2014 |
| EP | 2561128 B1 | 1/2015 |
| EP | 2829287 A1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |

(56) References Cited

FOREIGN PATENT DOCUMENTS

| | | |
|---|---|---|
| EP | 2438302 B1 | 9/2015 |
| EP | 2346545 B1 | 10/2015 |
| EP | 2438301 B1 | 10/2015 |
| EP | 2802304 B1 | 12/2015 |
| EP | 2852421 B1 | 1/2016 |
| EP | 2410962 B1 | 3/2016 |
| EP | 2640436 B1 | 3/2016 |
| EP | 2855937 B1 | 5/2016 |
| EP | 2433594 B1 | 6/2016 |
| EP | 2919730 B1 | 6/2016 |
| EP | 2861869 B1 | 7/2016 |
| EP | 2945584 B1 | 7/2016 |
| EP | 2293749 B1 | 8/2016 |
| EP | 3 072 542 | 9/2016 |
| EP | 2305327 B1 | 10/2016 |
| EP | 2467086 B1 | 10/2016 |
| EP | 2470135 B1 | 10/2016 |
| EP | 2767305 B1 | 10/2016 |
| EP | 2282788 B1 | 12/2016 |
| EP | 2462956 B2 | 3/2017 |
| EP | 3139878 A1 | 3/2017 |
| EP | 1587502 B1 | 5/2017 |
| EP | 1587554 B1 | 5/2017 |
| EP | 2731563 B1 | 5/2017 |
| EP | 2968871 B1 | 7/2017 |
| EP | 2632613 B1 | 8/2017 |
| EP | 2888478 B1 | 8/2017 |
| EP | 2937107 B1 | 8/2017 |
| EP | 2967627 B1 | 8/2017 |
| EP | 3062751 B1 | 8/2017 |
| EP | 3139879 B1 | 8/2017 |
| EP | 2359784 B1 | 9/2017 |
| EP | 3151795 B1 | 9/2017 |
| EP | 2367518 B1 | 10/2017 |
| EP | 2675493 B1 | 10/2017 |
| EP | 3068455 B1 | 10/2017 |
| EP | 2558046 B2 | 11/2017 |
| EP | 2736548 B1 | 11/2017 |
| EP | 3052158 B1 | 11/2017 |
| EP | 2593058 B1 | 3/2018 |
| EP | 3139880 B1 | 3/2018 |
| EP | 1496822 B1 | 8/2018 |
| EP | 2879633 B1 | 8/2018 |
| EP | 2227203 B1 | 9/2018 |
| EP | 2696826 B1 | 9/2018 |
| EP | 3106186 B1 | 9/2018 |
| EP | 3162330 B1 | 9/2018 |
| EP | 3169382 B1 | 9/2018 |
| EP | 3203953 B1 | 9/2018 |
| EP | 2941280 B1 | 10/2018 |
| EP | 3244852 B1 | 10/2018 |
| EP | 3062753 B1 | 11/2018 |
| EP | 3120879 B1 | 12/2018 |
| EP | 3191149 B1 | 1/2019 |
| EP | 2370130 B1 | 3/2019 |
| EP | 3053609 B1 | 3/2019 |
| EP | 3180048 B1 | 3/2019 |
| EP | 3143974 B1 | 4/2019 |
| EP | 2285432 B2 | 6/2019 |
| EP | 3050545 B1 | 7/2019 |
| EP | 3319656 B1 | 8/2019 |
| EP | 2355762 B1 | 9/2019 |
| EP | 2822613 B1 | 9/2019 |
| EP | 2863855 B1 | 9/2019 |
| EP | 2482912 B1 | 10/2019 |
| EP | 3038667 B1 | 10/2019 |
| EP | 3129095 B1 | 10/2019 |
| EP | 3191150 B1 | 10/2019 |
| EP | 3280466 B1 | 10/2019 |
| EP | 2244756 B1 | 12/2019 |
| EP | 2968702 B1 | 12/2019 |
| FR | 2 939 320 | 6/2010 |
| GB | 2511523 | 9/2014 |
| JP | H04-354722 | 12/1992 |
| RU | 131622 | 8/2013 |
| WO | WO 2009/098696 | 8/2009 |
| WO | WO 2009/120951 | 10/2009 |
| WO | WO 2011/049562 | 4/2011 |
| WO | WO 2011/130570 | 10/2011 |
| WO | WO 2011/135285 | 11/2011 |
| WO | WO 2011/146532 | 11/2011 |
| WO | WO-2011144888 A1 | 11/2011 |
| WO | WO 2013/175306 | 11/2013 |
| WO | WO 2014/099709 | 6/2014 |
| WO | WO 2016/103031 | 6/2016 |
| WO | WO-2016126560 A1 | 8/2016 |
| WO | WO 2016/182977 | 11/2016 |
| WO | WO 2017/079174 | 5/2017 |
| WO | WO 2017/153357 | 9/2017 |
| WO | WO 2017/186771 | 11/2017 |
| WO | WO 2017/191154 | 11/2017 |
| WO | WO-2017196888 A1 | 11/2017 |
| WO | WO 2018/037075 | 3/2018 |
| WO | WO-2018056060 A1 | 3/2018 |
| WO | WO-2018115461 A1 | 6/2018 |
| WO | WO-2018156730 A1 | 8/2018 |
| WO | WO 2018/164803 | 9/2018 |
| WO | WO-2018158250 A1 | 9/2018 |
| WO | WO-2018162613 A1 | 9/2018 |
| WO | WO 2018/187394 | 10/2018 |
| WO | WO-2018185138 A1 | 10/2018 |
| WO | WO-2018192978 A1 | 10/2018 |
| WO | WO-2018206420 A1 | 11/2018 |

OTHER PUBLICATIONS

Owen, M.J. Silicone Hydrophobicity and Oleophilicity. Silicon 9, 651-655 (2017). https://doi.org/10.1007/s12633-014-9188-0 (Year: 2017).*

International Search Report and Written Opinion, re PCT Application No. PCT/EP2017/071322, dated Nov. 30, 2017.

International Search Report and Written Opinion, re PCT Application No. PCT/EP2016/059329, dated Jul. 14, 2016.

International Preliminary Report on Patentability for Application No. PCT/EP2017/071322, dated Mar. 7, 2019, 13 pages.

* cited by examiner

ABSORBENT NEGATIVE PRESSURE WOUND THERAPY DRESSING

CROSS-REFERENCE TO RELATED APPLICATIONS

This application is a U.S. national stage application of International Patent Application No. PCT/EP2017/071322, filed Aug. 24, 2017, which claims priority to U.S. Provisional Application No. 62/379,667, filed Aug. 25, 2016, which is hereby incorporated by reference in its entirety.

BACKGROUND

Technical Field

Disclosed embodiments relate generally to the treatment of wounds using negative pressure wound therapy, in particular the prevention of fluid absorption in selected regions of a negative pressure wound therapy dressing.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

However, in some wound dressings the absorbent layer fills up with fluid in an unpredictable, and often, non-uniform manner. It may be desirable, in some situations, to more easily prevent fluid from reaching certain areas of the wound dressing and/or certain portions of the absorbent layer. Current dressings have limited and/or unsatisfactory methods of controlling fluid paths in the absorbent layer.

SUMMARY

Embodiments of this disclosure include wound dressing apparatuses and methods of manufacturing and utilizing the same. Particular embodiments are directed to wound dressing apparatuses and methods of using the same having an absorbent area for retaining wound exudate within the wound dressing, and a negative pressure source in fluid communication with the absorbent area. The negative pressure source may be connected to the wound dressing via a connector attached to the wound dressing, or the negative pressure source may be on or within the wound dressing itself.

According to some embodiments, there is provided a wound dressing including a wound contact layer configured to be positioned in contact with a wound; a first area over the wound contact layer that includes a lower spacer layer and an absorbent layer; a second area over the wound contact layer that includes an optional plurality of spacer layers and a negative pressure source and/or electronic components positioned within or between the plurality of spacer layers, wherein the first area is positioned adjacent to the second area and separated by a partition, wherein the partition is formed by an epoxy material applied to one or more layers of the first area and/or the second area; and a cover layer configured to cover and form a seal over the wound contact layer, the first area, and the second area.

Wound dressing of the preceding paragraph can include one or more of the following features. In some embodiments of a wound dressing, the epoxy material includes a flexible hydrophobic material. In some embodiments of a wound dressing, the epoxy material includes a silicone adhesive. In embodiments, the wound treatment may further include an upper spacer layer configured to cover the first area and the second area and to allow air to be communicated between the first area and second area around the partition. In some embodiments of a wound dressing, the plurality of spacer layers in the second area include a third spacer layer beneath the negative pressure source and/or electronic components and a fourth spacer layer positioned above the negative pressure source and/or electronic components, wherein the fourth spacer layer includes one or more cutouts or recesses configured to receive the negative pressure source and/or electronic components. In embodiments, the wound treatment apparatus may further include one or more user interface components configured to allow a user to operate the negative pressure source and/or electronic components.

According to another embodiment there is provided, a wound dressing including a wound contact layer configured to be positioned in contact with a wound; a first area over the wound contact layer that includes a lower spacer layer and an absorbent layer; a second area over the wound contact layer including an optional plurality of layers and a negative pressure source and/or electronic components positioned within or between the plurality of layers, wherein the first area is positioned adjacent to the second area; and wherein one or more layers of the plurality of layers of the second area include a hydrophobic material surrounding the negative pressure source and/or electronic components; and a cover layer configured to cover and form a seal over the wound contact layer, the first area, and the second area.

Wound dressings of any of the preceding paragraphs can include one or more of the following features. In some embodiments of a wound dressing, the absorbent layer includes a portion adjacent to the second area and wherein the portion adjacent to the second area includes a hydrophobic material. In certain embodiments, the wound treatment apparatus may further include an upper spacer layer configured to cover the first area and the second area and to allow air to be communicated between the first area and second area. In some embodiments, the wound dressing the plurality of layers in the second area include a third spacer layer beneath the negative pressure source and/or electronic components and a fourth spacer layer positioned above the negative pressure source and/or electronic components, wherein the fourth spacer layer includes one or more cutouts or recesses configured to receive the negative pressure source and/or electronic components. In some embodiments, the wound dressing wherein the plurality of layers in the second area include a third spacer layer beneath the negative pressure source and/or electronic components, wherein the third spacer layer and the lower spacer layer are one continuous layer positioned below the absorbent layer and the negative pressure source and/or electronic components and above the wound contract layer. In embodiments, the wound treatment apparatus may further include one or more user interface components configured to allow a user to operate the negative pressure source and/or electronic components.

DETAILED DESCRIPTION

Figure 1A:
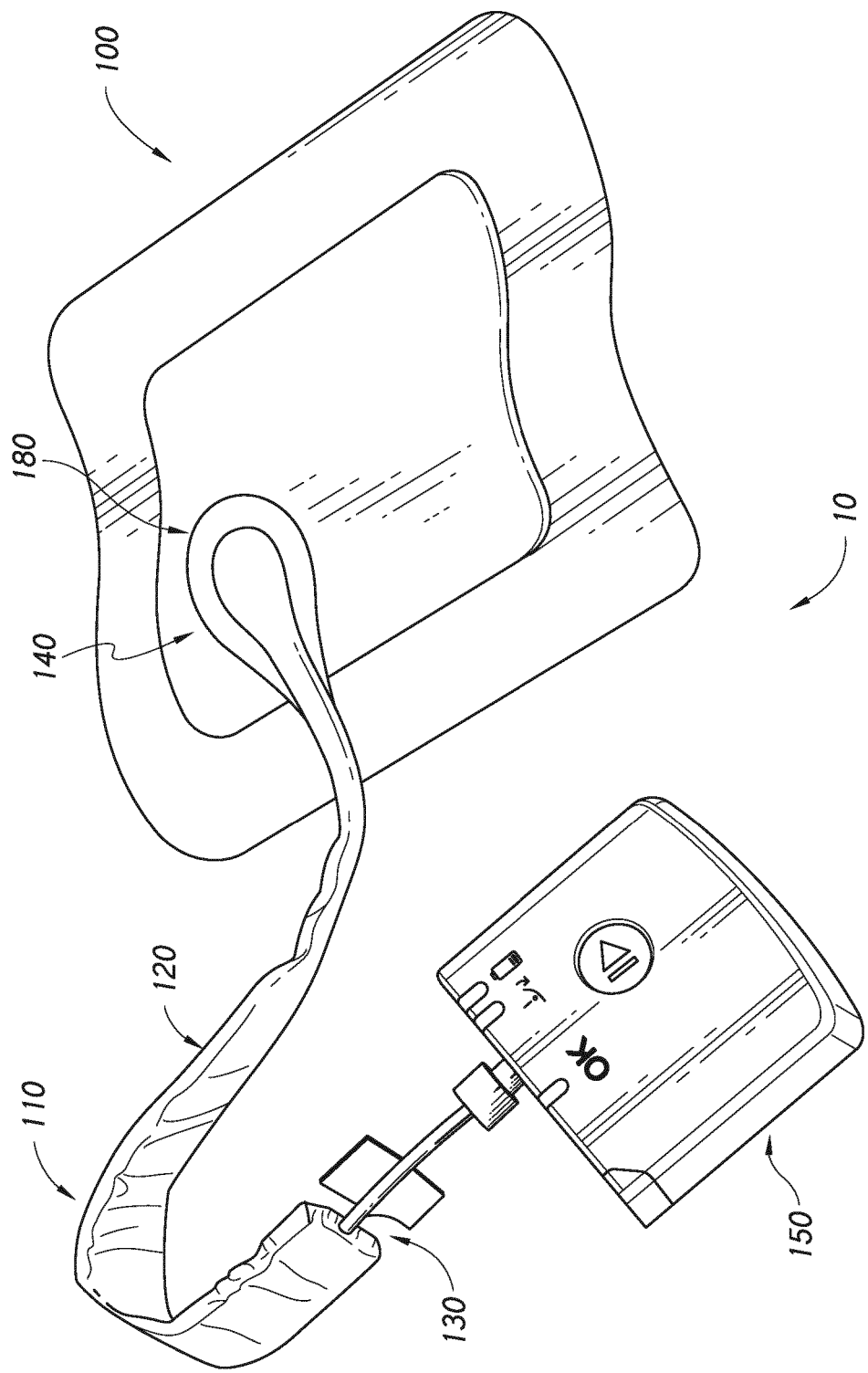
FIG. 1A illustrates an embodiment of a negative pressure wound treatment system employing a flexible fluidic connector and a wound dressing capable of absorbing and storing wound exudate.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

Some embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. Wounds include, but are not limited to, open wounds, incisions, lacerations, abrasions, contusions, burns, diabetic ulcers, pressure ulcers, stoma, surgical wounds, trauma and venous ulcers or the like. Treatment of such wounds can be performed using negative pressure wound therapy, wherein a reduced or negative pressure can be applied to the wound to facilitate and promote healing of the wound. It will also be appreciated that the fluidic connector and methods as disclosed herein may be applied to other parts of the body, and are not necessarily limited to treatment of wounds.

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds. Certain embodiments of this application relate to a wound treatment apparatus employing a wound dressing and a fluidic connector, and to methods of using the same.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as $-X$ mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of $-X$ mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., $-40$ mmHg is less than $-60$ mmHg). Negative pressure that is "more" or "greater" than $-X$ mmHg corresponds to pressure that is further from atmospheric pressure (e.g., $-80$ mmHg is more than $-60$ mmHg). In some embodiments, local ambient atmospheric pressure is used as a reference point, and such local atmospheric pressure may not necessarily be, for example, 760 mmHg.

The negative pressure range for some embodiments of the present disclosure can be approximately $-80$ mmHg, or between about $-20$ mmHg and $-200$ mmHg Note that these pressures are relative to normal ambient atmospheric pressure, which can be 760 mmHg Thus, $-200$ mmHg would be about 560 mmHg in practical terms. In some embodiments, the pressure range can be between about $-40$ mmHg and $-150$ mmHg. Alternatively a pressure range of up to $-75$ mmHg, up to $-80$ mmHg or over $-80$ mmHg can be used. Also in other embodiments a pressure range of below $-75$ mmHg can be used. Alternatively, a pressure range of over approximately −100 mmHg, or even −150 mmHg, can be supplied by the negative pressure apparatus.

Figure 1B:
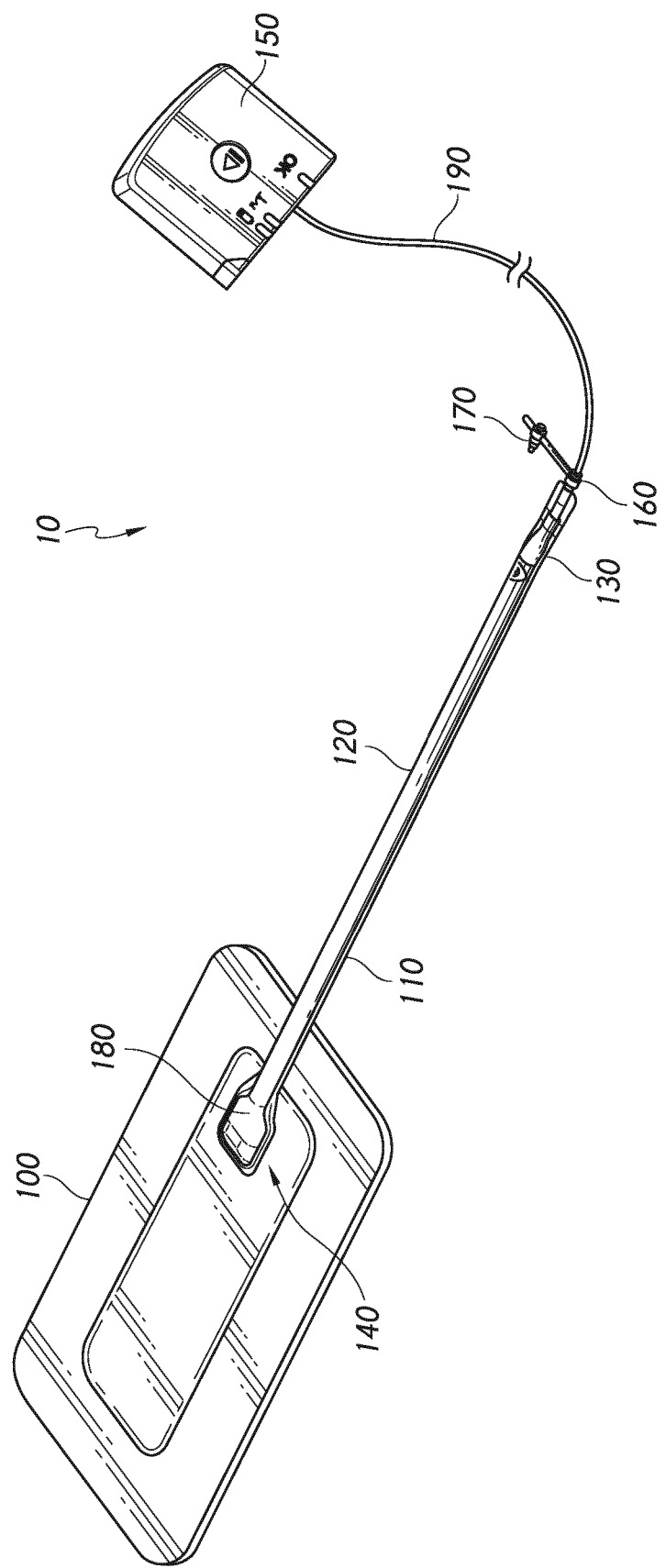
FIG. 1B illustrates an embodiment of a negative pressure wound treatment system employing a flexible fluidic connector and a wound dressing capable of absorbing and storing wound exudate.

FIGS. 1A-B illustrate embodiments of a negative pressure wound treatment system 10 employing a wound dressing 100 in conjunction with a fluidic connector 110. Here, the fluidic connector 110 may include an elongate conduit, more preferably a bridge 120 having a proximal end 130 and a distal end 140, and an applicator 180 at the distal end 140 of the bridge 120. In some embodiments, an optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may include a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Figure 2A:
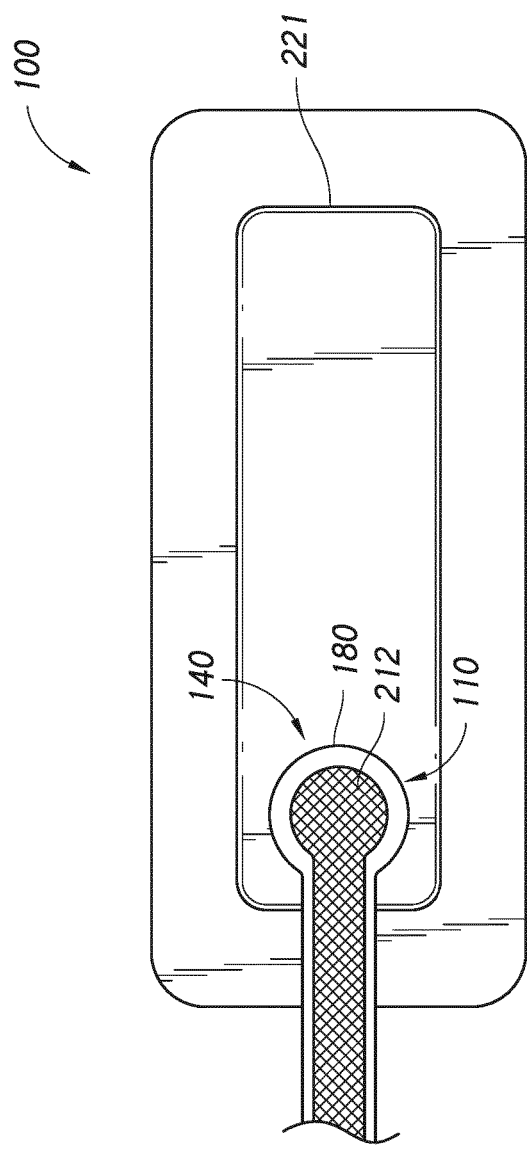
FIG. 2A illustrates an embodiment of a negative pressure wound treatment system employing a flexible fluidic connector and a wound dressing capable of absorbing and storing wound exudate.
Figure 2B:
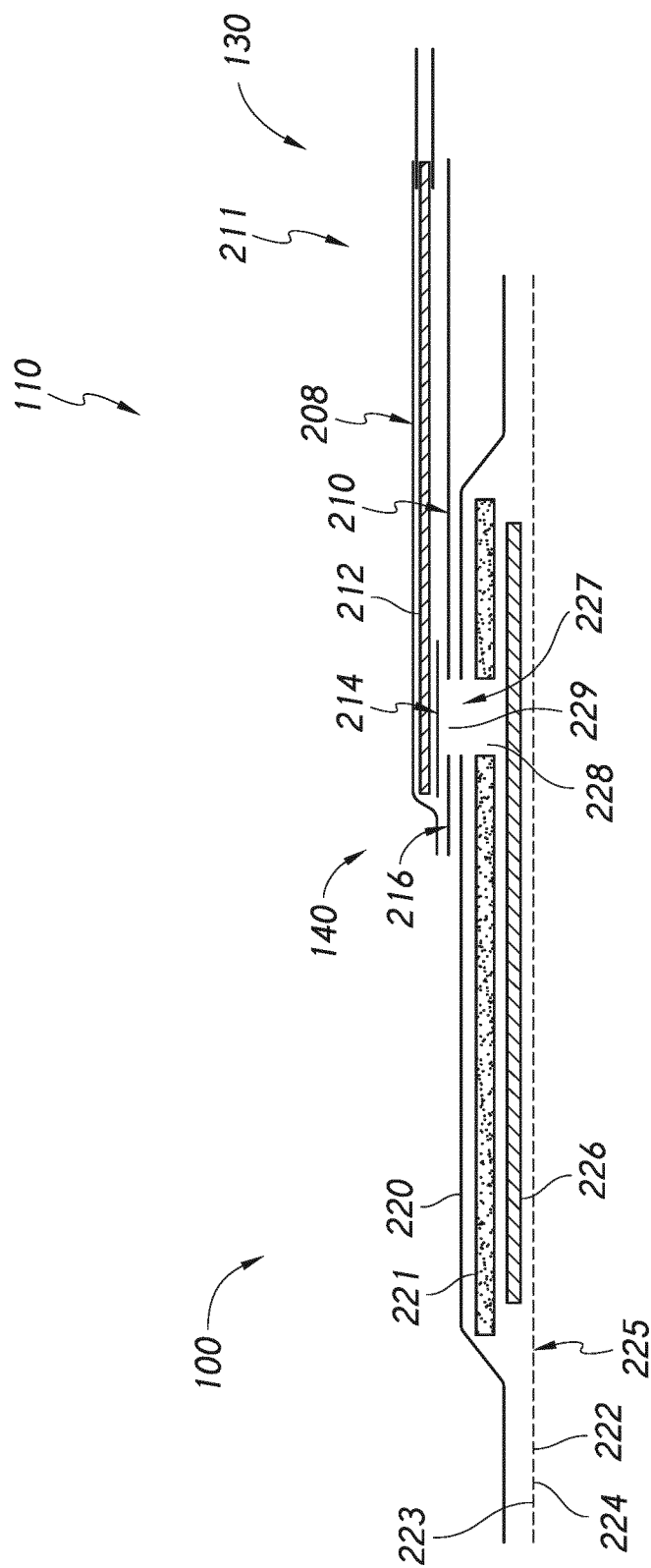
FIG. 2B illustrates a cross section of an embodiment of a fluidic connector connected to a wound dressing.

With reference initially to FIGS. 2A-B, treatment of a wound with negative pressure in certain embodiments of the application uses a wound dressing 100 capable of absorbing and storing wound exudate in conjunction with a flexible fluidic connector 110. In some embodiments, the wound dressing 100 may be substantially similar to wound dressings and have the same or similar components as those described throughout International Patent Publication WO2013175306, WO2014020440, WO2014020443 and U.S. Publication No. 2011/0282309 A1, which are incorporated by reference in their entireties. In other embodiments (not shown), the wound dressing may simply include one or more backing layers configured to form a sealed chamber over the wound site. In some embodiments, it may be preferable for the wound site to be filled partially or completely with a wound packing material. This wound packing material is optional, but may be desirable in certain wounds, for example deeper wounds. The wound packing material can be used in addition to the wound dressing 100. The wound packing material generally may include a porous and conformable material, for example foam (including reticulated foams), and gauze. In some embodiments, preferably, the wound packing material is sized or shaped to fit within the wound site so as to fill any empty spaces. The wound dressing 100 may then be placed over the wound site and wound packing material overlying the wound site. When a wound packing material is used, once the wound dressing 100 is sealed over the wound site, negative pressure may be transmitted from a pump or other source of negative pressure through a flexible tubing via the fluidic connector 110 to the wound dressing 100, through the wound packing material, and finally to the wound site. This negative pressure draws wound exudate and other fluids or secretions away from the wound site.

As shown in the embodiment of FIG. 2A, the fluidic connector 110 preferably includes an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may include two or more fluidic connectors 110, each comprising one or more heads 140, in fluidic communication therewith. In some embodiments, the head 140 may preferably measure 30 mm along its widest edge. The head 140 forms at least in part the applicator 180, described above, that is configured to seal against a top surface of the wound dressing.

FIG. 2B illustrates a cross-section through a wound dressing 100 similar to the wound dressing 10 as shown in FIG. 1B and described in International Patent Publication WO2013175306, which is incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed so as to form a sealed cavity over the wound site. In a some embodiments, the dressing 100 preferably includes a top or cover layer, or backing layer 220 attached to an optional wound contact layer 222, both of which are described in greater detail below. These two layers 220, 222 are preferably joined or sealed together so as to define an interior space or chamber. This interior space or chamber may include additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As illustrated in FIG. 2B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. In some embodiments, the perforations 225 preferably include through holes in the wound contact layer 222 which enable fluid to flow through the layer 222. The wound contact layer 222 helps prevent tissue ingrowth into the other material of the wound dressing. In certain embodiments, preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may include perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In certain embodiments, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 includes a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

In some embodiments, preferably, to improve the liquid flow across the transmission layer 226 (that is to say perpendicular to the channel region formed between the top and bottom spacer layers) the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which include a foam or non-woven natural or synthetic material, and which may optionally include a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing. In some embodiments, the material of the absorbent layer 221 preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudate flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™11C-450. In some embodiments, the absorbent layer 221 may include a composite comprising superabsorbent powder, fibrous material such as cellulose, and bonding fibers. In certain embodiments, a preferred composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

In some embodiments, an aperture, hole, or orifice 227 is preferably provided in the backing layer 220 to allow a negative pressure to be applied to the dressing 100. In certain embodiments, the fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

In some embodiments, the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 2B a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 can be provided in the absorbent layer 221 beneath the orifice 227 such that the orifice is connected directly to the transmission layer 226. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440 may be provided over the absorbent layer 221 and beneath the backing layer 220.

In some embodiments, the backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. In certain embodiments, the backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. In some implementations, the backing layer 220 preferably includes two layers; a polyurethane film and an adhesive pattern spread onto the film. In certain embodiments, the polyurethane film is preferably moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. In some embodiments, the transmission layer 226 can be a greater area than the absorbent layer 221, such that the transmission layer 226 extends beyond the edges of the absorbent layer 221. The dressing can include one or more transmission layers positioned above or below the absorbent layer. As illustrated in FIGS. 2A-2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 100 includes an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

In particular for some embodiments with a single fluidic connector 110 and through hole, it may be preferable for the fluidic connector 110 and through hole to be located in an off-center position as illustrated in FIG. 2A. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Turning now to the fluidic connector 110, some embodiments preferably include a sealing surface 216, a bridge 211 (corresponding to bridge 120 in FIGS. 1A-1B) with a proximal end 130 and a distal end 140, and a filter 214. In certain embodiments, the sealing surface 216 preferably forms the applicator previously described that is sealed to the top surface of the wound dressing. In some embodiments a bottom layer of the fluidic connector 110 may include the sealing surface 216, such as layer 540 in FIG. 5C below. The fluidic connector 110 may further include an upper surface vertically spaced from the sealing surface 216, which in some embodiments is defined by a separate upper layer of the fluidic connector such as layer 510 in FIG. 5C below. In other embodiments the upper surface and the lower surface may be formed from the same piece of material. In some embodiments the sealing surface 216 may include at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may include an adhesive or weld. In some embodiments, the sealing surface 216 may be placed over an orifice in the cover layer. In some embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may include a first fluid passage 212 in communication with a source of negative pressure, the first fluid passage 212 comprising a porous material, such as a 3D knitted material, which may be the same or different than the porous layer 226 described previously. In some embodiments, the bridge 211 is preferably encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge. These elements will be described in greater detail below.

Some embodiments may further include an optional second fluid passage positioned above the first fluid passage 212. For example, some embodiments may provide for an air leak may be disposed at the proximal end of the top layer that is configured to provide an air path into the first fluid passage 212 and dressing 100, similar to the suction adapter described in U.S. Pat. No. 8,801,685, which is incorporated by reference herein in its entirety.

In some embodiments, preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may include several layers of material stacked or layered over each other, which may in some cases be useful in preventing the fluid passage 212 from collapsing under the application of negative pressure. In certain embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm Some embodiments, for example a suction adapter used with a dressing which retains liquid such as wound exudate, may employ hydrophobic layers in the fluid passage 212, and only gases may travel through the fluid passage 212. Additionally, and as described previously, the materials used in some embodiments of the system are preferably conformable and soft, which may help to avoid pressure ulcers and other complications which may result from a wound treatment system being pressed against the skin of a patient.

In some embodiments, preferably, the filter element 214 is impermeable to liquids, but permeable to gases, and is provided to act as a liquid barrier and to ensure that no liquids are able to escape from the wound dressing 100. The filter element 214 may also function as a bacterial bather. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable in some embodiments, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments, filter element 214 includes a support layer and an acrylic co-polymer membrane formed on the support layer. Preferably the wound dressing 100 according to certain embodiments uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

Pump and Electronics on Dressing

Figure 2C:
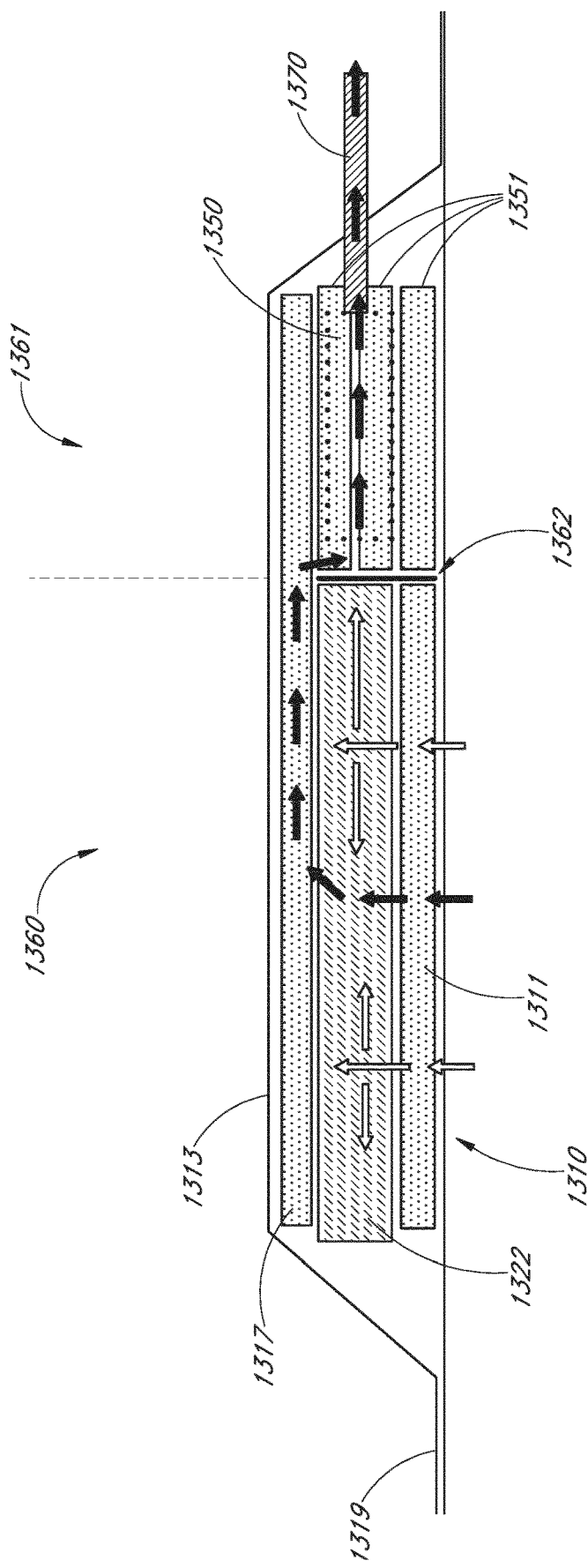
FIG. 2C illustrates a wound dressing with the pump and/or other electronics positioned away from the wound site according to an embodiment.

In some embodiments, a pump and/or other electronic components can be configured to be positioned adjacent to or next to the absorbent and/or transmission layers so that the pump and/or other electronic components are still part of a single apparatus to be applied to a patient, but the pump and/or other electronics are positioned away from the wound site. In some embodiments, a pump and/or other electronic components can be positioned above or mounted above the absorbent and/or transmission layers described above. FIG. 2C illustrates a wound dressing with the pump and/or other electronics positioned away from the wound site. The wound dressing can include an electronics area 1361 and an absorbent area 1360. The absorbent area 1360 can include an absorbent material and can be positioned over the wound site. The electronics area 1361 can be positioned away from the wound site, such as by being located off to the side from the absorbent area 1360. The electronics area 1361 can be positioned adjacent to and in fluid communication with the absorbent area 1360. In some embodiments, each of the electronics area 1361 and absorbent area 1360 may be rectangular in shape, and positioned adjacent to one another. The electronics can be located in the electronics area 1361, and the absorbent area 1360 can be placed on the wound. The dressing can include a wound contact layer 1310, one or more spacer or transmission layers 1311 and/or 1317, an absorbent layer 1322, a moisture vapor permeable film or cover layer 1313 positioned above the contact layer, one or more spacer layers, absorbent layer, or other layers of the dressing. The wound contact layer 1310, one or more spacer or transmission layers 1311 and/or 1317, an absorbent layer 1322, a moisture vapor permeable film or cover layer 1313 can include similar materials and characteristics as described with reference to the corresponding wound contact layer, spacer or transmission layer, absorbent layer, and cover layer described with reference to FIGS. 2A-2B. The wound dressing layers of the electronics area and the absorbent layer can be covered by one continuous cover layer 1313.

FIG. 2C illustrates an embodiment of a wound dressing with the pump and electronic components offset from the absorbent area of the dressing positioned over the wound. The wound dressing can include a wound contact layer 1310 and a moisture vapor permeable film or cover layer 1313 that enclose an absorbent area 1360 and an electronics area 1361. The cover layer 1313 can seal at the perimeter of the cover layer 1319 to the wound contact layer 1310 at the perimeter of the wound contact layer. The dressing can include an upper spacer layer or first spacer layer 1317 that includes a continuous layer of spacer material positioned below the cover layer 1313 and above the layers of the absorbent area and the layers of the electronics area. The continuous layer of spacer material or upper spacer layer 1317 can enable an air pathway between the two areas of the dressing. In some embodiments, the spacer layer 1317 is only provided over the absorbent area 1360 and does not extend over the electronics area 1361.

The absorbent area 1360 of the dressing can include a second spacer layer 1311 or lower spacer layer and an absorbent layer 1322 positioned above the wound contact layer 1310. The second spacer layer 1311 can allow for an open air path over the wound site. The absorbent layer 1322 can include a super absorber positioned in the absorbent area 1360 of the dressing. The absorbent layer 1322 can retain wound fluid within thereby preventing fluid passage of wound exudates into the electronics area 1361 of the dressing. The wound fluids can flow through the wound contact layer 1310, to the lower spacer layer 1311, and into the absorbent layer 1322. The wound fluids are then spread throughout the absorbent layer 1322 and retained in the absorbent layer 1322 as shown by the directional arrows for wound fluids in FIG. 2C.

The electronics area 1361 of the dressing can include a plurality of layers of spacer material 1351 and electronic components 1350 embedded within the plurality of layers of spacer material 1351. The layers of spacer material can have recesses or cut outs to embed the electronic components within whilst providing structure to prevent collapse. The electronic components 1350 can include a pump, power source, controller, and/or an electronics package.

In some embodiments, a partition, divider, and/or other separating material or device can be positioned between the absorbent area and the electronics area. In some embodiments, the separating material can be a partition 1362 as shown in FIG. 2C. In some embodiments, the partition 1362 can be positioned between the absorbent area 1360 and the electronics area 1361. The partition 1362 can separate the absorbent layer 1322 and lower air flow spacer layer 1311 from the electronic housing segment of the dressing in the electronic area. The partition 1362 can prevent wound fluid from entering the electronic housing section of the dressing. In some embodiments, the partition can be a non-porous dam or other structure. The non-porous dam 1362 can include a cyanoacrylate adhesive bead or a strip of silicone. The air pathway through the dressing is shown in FIG. 2C by directional arrows. The air flows through the wound contact layer 1310, the lower spacer layer 1311, and the absorbent layer 1322 and into the first spacer layer 1317. The air can travel horizontally through the first spacer layer 1317 over and around the partition 1362 into the electronics area of the dressing.

A pump exhaust 1370 can be provided to exhaust air from the pump to the outside of the dressing. The pump exhaust can be in communication with the electronics area 1361 and the outside of the dressing. In some embodiments, the pump exhaust 1370 can be a flexible fluidic connector that includes a 3D material that allows for pressure to be applied without collapse of the exhaust port. Examples of an application where additional disclosure relating to the 3D material can be found include US Publication No. 2015/0141941, titled "Apparatuses and Methods for Negative Pressure Wound Therapy" published on May 21, 2015. The disclosure of this patent is hereby incorporated by reference in its entirety.

Application of Glue to Dressing

In certain embodiments, such as described above in FIG. 2B, fluid (for example, wound exudate) is handled by the dressing 100 by passing through the perforated wound contact layer 222, into the transmission layer 226, and is then absorbed and retained by the absorbent layer 221. Fluid is then able to evaporate through the breathable backing layer 220. However, in some embodiments, such as those observed during in vitro wound model testing, the absorbent layer fills up with the fluid in an unpredictable, and often, non-uniform manner Therefore, as described above, it may be desirable to prevent fluid from reaching certain areas of the absorbent layer.

In certain embodiments, fluid saturation of the absorbent layer may be impeded by applying a glue such as a cyanoacrylate Super Glue (for example Loctite, by Henkel) onto the backing layer. Herein this section and throughout the specification, the term "glue" will be used to indicate an adhesive such as Super Glue or any cyanoacrylate glue. Application of the glue affects the underlying absorbent layer by preventing fluid from being absorbed in the area below the glue. In some embodiments, the glue prevents certain areas of the absorbent material from swelling with fluid. Glue may be applied to the backing layer or elsewhere in the dressing via any suitable method, such as via an applicator tube.

Figure 3:
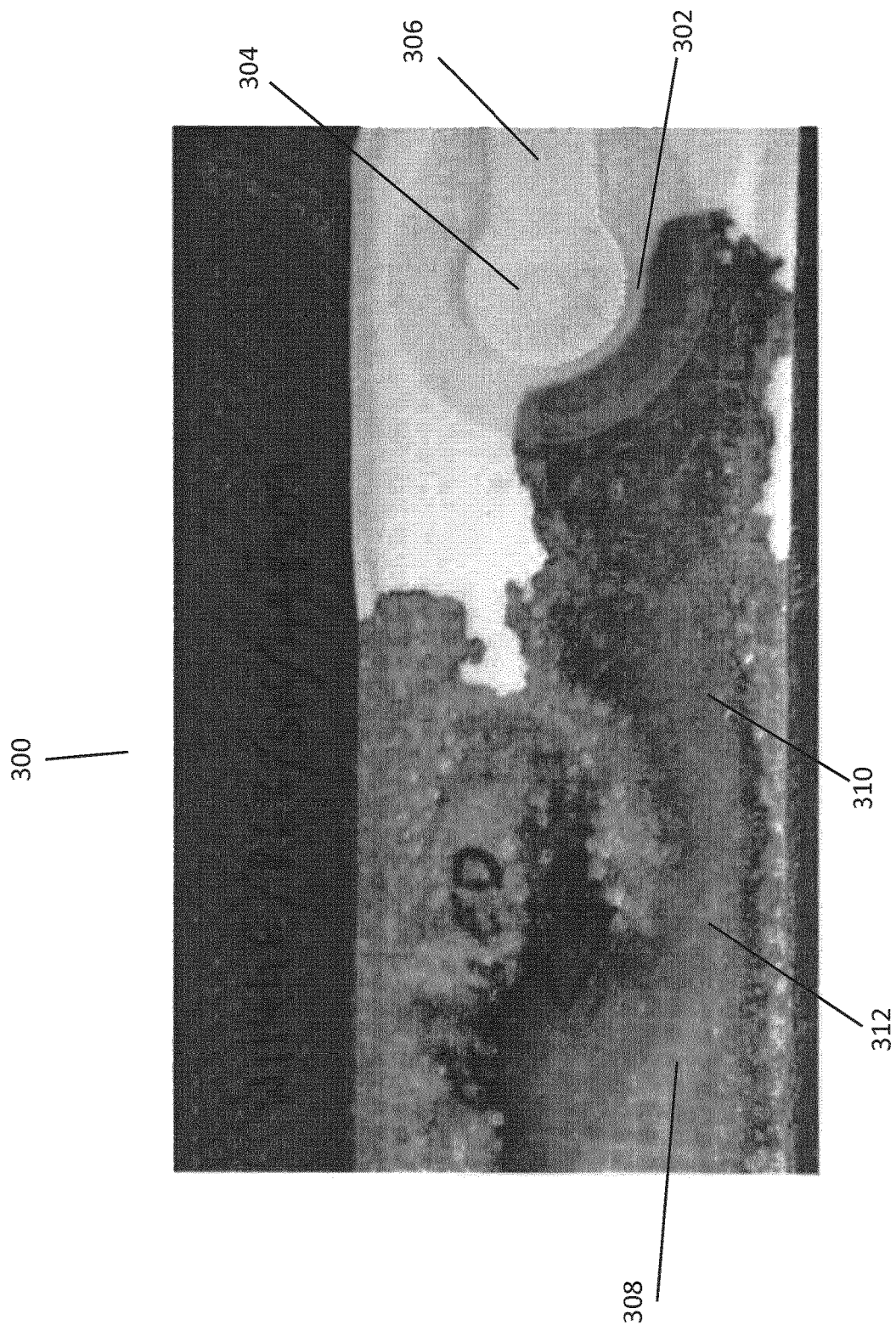
FIG. 3 is an image of an embodiment of a partially saturated wound dressing, comprising a ring of glue around the distal end of a fluidic connector.

Turning to FIG. 3, showing a top view of an embodiment of a wound dressing 300, similar to the dressings described in FIGS. 2A-2B, a ring of glue 302 adheres the distal end 304 of the fluidic connector 306 to dressing 300. Fluid was drawn into the dressing 308 and is visible through the backing layer 310 saturating the absorbent layer 312. However, the fluid bends around the ring of glue 302, even though the glue has been applied to the top of the backing layer 312. In embodiments, application of glue to the top of the backing layer may beneficially prevent areas of the underlying absorbent layer 312 from becoming saturated and swelling. In embodiments, this prevention of saturation is beneficial as swelling of super absorber particles in this area can occlude the fluidic connection 306, therefore preventing negative pressure delivery.

In certain embodiments, the glue may be located at a variety of locations on the backing layer. For example, the glue may be applied all the way to the edge of the opening in the backing layer and/or cover the entire distal end of the fluidic connector to the outer edge of the fluidic connector. As described above, the glue may be applied around the rim of the opening in the form of a ring. In embodiments, the glue may be applied as a single line or as a series of lines. The glue may be applied as a spiral or as concentric circles on the backing layer. In certain embodiments, the glue may be applied as distinct, single lines or multiple lines. The glue may be applied to the underside of the backing layer in any manner described in relation to the topside of the backing layer.

In embodiments, the glue may be applied around the periphery of the backing layer, for example, the entire periphery, 50% of the entirety, or 25% of the entirety. In certain embodiments the glue may be applied to only a portion of the perimeter of the distal end fluidic connector, for example 25%, 50%, or 75%. The glue may be applied to create channels in the underlying absorbent layers to channel wound exudate to the opening in the backing layer. In certain embodiments, the glue may be applied under the applicator portion of the fluidic connector, but not the fluid passage. In embodiments, the glue may be applied to only the outermost ring of the applicator portion of the fluidic connector. In certain embodiments, the glue may be applied to the sealing surface of the fluidic connector. In further embodiments, the glue may be applied on the backing layer around but not under the fluidic connector.

In certain embodiments, the glue may be applied directly to the absorbent layer in any manner described herein this section or elsewhere in the specification, particularly as described above in relation to the backing layer. In some embodiments, the glue may be applied directly to the transmission layer in any manner described herein this section or elsewhere in the specification, particularly as described above in relation to the backing layer. In embodiments, the glue may be applied directly to the wound contact layer in any manner described herein this section or elsewhere in the specification, particularly as described above in relation to the backing layer.

Figure 4:
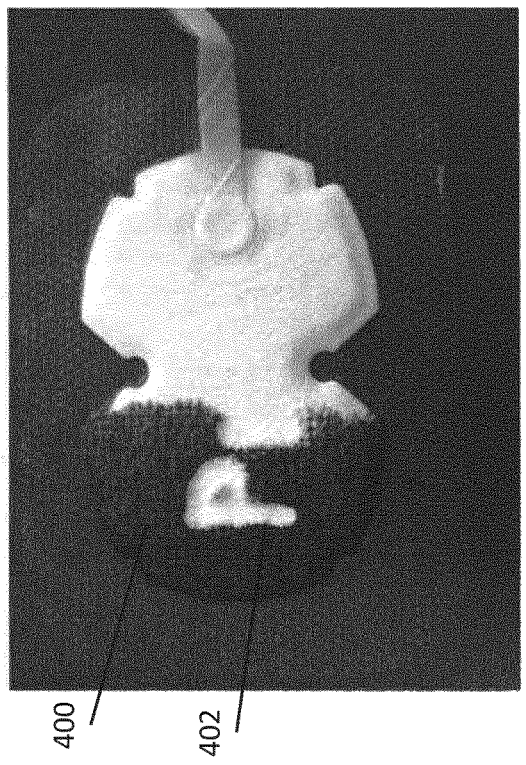
FIG. 4 shows multiple images of embodiments of a wound dressing that becomes more saturated with dyed fluid over time.
Figure 4:

FIG. 4 shows two images of an embodiment of a wound dressing 400, similar to the dressings of FIGS. 2A-3. Here, a thin bead of super glue was used to write "PICO" on the dressing 402, specifically to the top of the backing layer. The dressing was then filled with a dye solution 404 which gradually revealed the word "PICO" written on the backing layer of the dressing. Similar to the glue ring shown in FIG. 3, application of glue to the top of the backing layer prevented areas of the underlying absorbent layer from becoming saturated. In certain embodiments, application of glue may be used to purposefully prevent areas of an absorbent layer (for example, around the distal end of the fluidic connector) from becoming saturated.

FIGS. 5-8 are images of embodiments of dressings similar to the dressings of FIGS. 2A-4. The dressings were sectioned using a clean pair of scissors and a single edge razor blade. These images were motivated by certain observations of in vitro wound dressings. After application of glue to the port of a PICO dressing, it was observed that in a wound model the glued area appeared to repel horse serum, which would normally track to the port and block the port, often before the dressing was full. For the above observation, the glue was applied between the port and the top film of the dressing and around the cut edges of a hole in the absorbent layer directly underneath the soft port.

Figure 5:
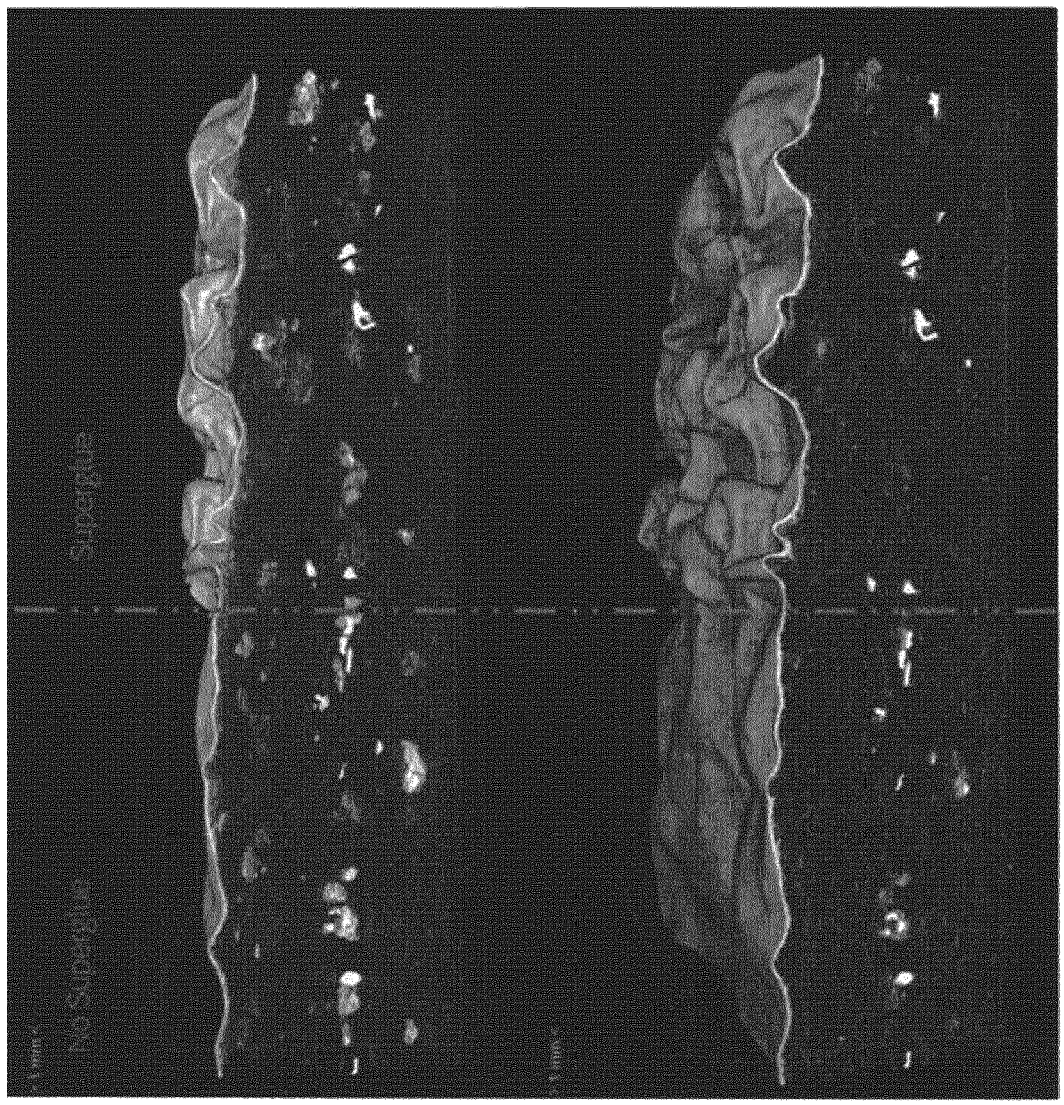
FIG. 5 shows multiple cross-sectional micro-CTs of embodiments of wound dressings with glue on the backing layer.

FIG. 5 shows micro-CT images, at two cross-sectional angles, of embodiments of a dressing 500 similar to the dressings of FIGS. 2A-4. Here, glue applied over the backing layer of a dressing is compared side-by-side with a backing layer with no glue. Apart from the textured appearance of the top film on the glue areas there were no macro structural differences between the areas with and without glue, in that there is no distinct sign of the fibers being bound together.

Figure 6:
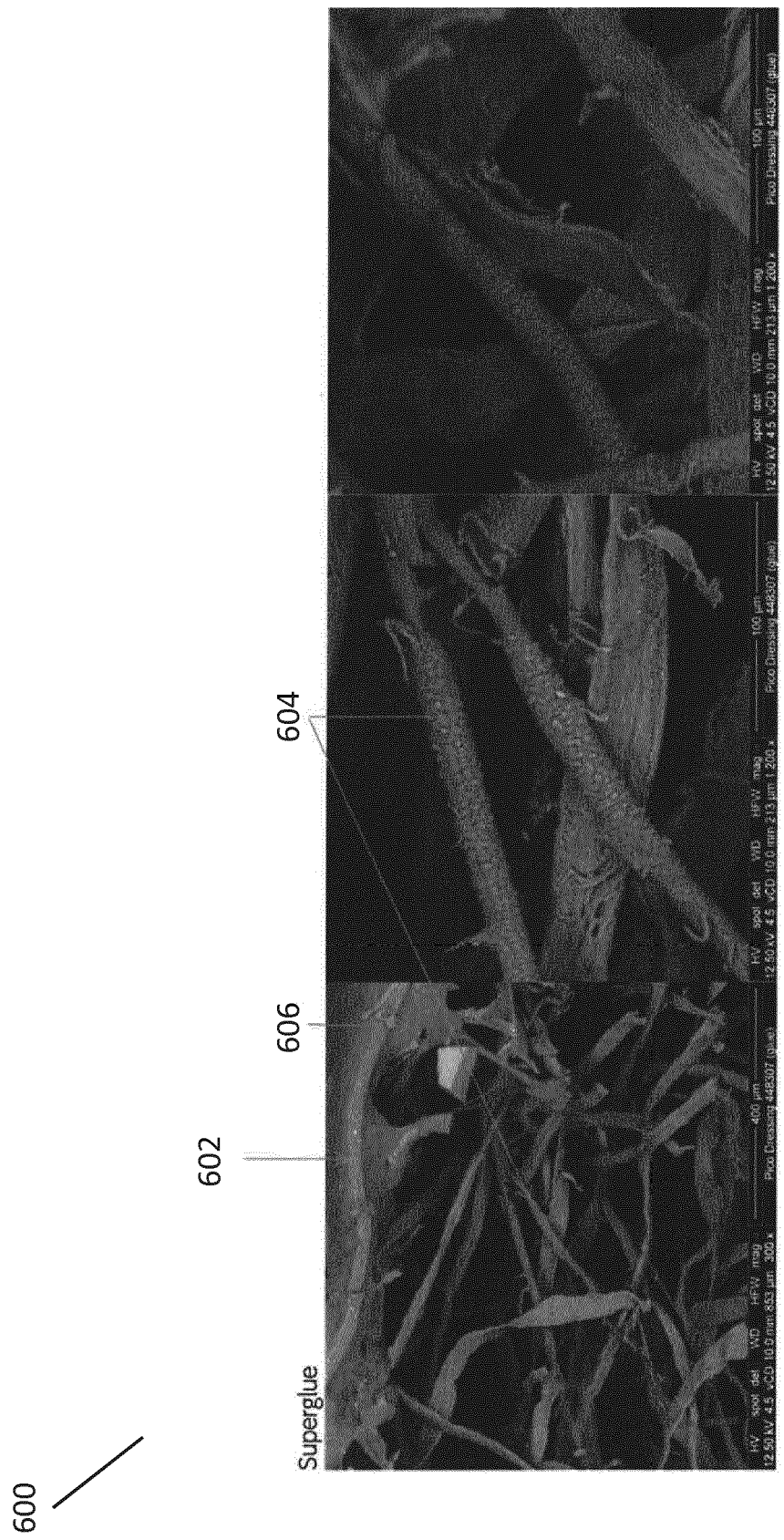
FIG. 6 shows multiple scanning electron microscopy (SEM) micrographs of embodiments of wound dressings with glue on the backing layer.

FIG. 6 is a series of SEM images of an embodiment of a dressing similar to the dressings of FIGS. 2-5. Here, the backing layer was coated in glue 602. Inspection of the dressing section coated with glue did show that under the backing layer (with the glue) there were a number of fibers 604 and a section of a superabsorber particle (shown in FIG. 7) which had been coated with granular particulates. The granular particulates were not observed on the flat cellulosic fibers. Chemical analysis would be required to determine if there is a thin film of glue on the flat fibers (i.e. fibers where granular particulates were not seen by SEM). FIG. 6 further includes construction adhesive 606 which was identified based on previous knowledge of similar dressings.

Figure 7:
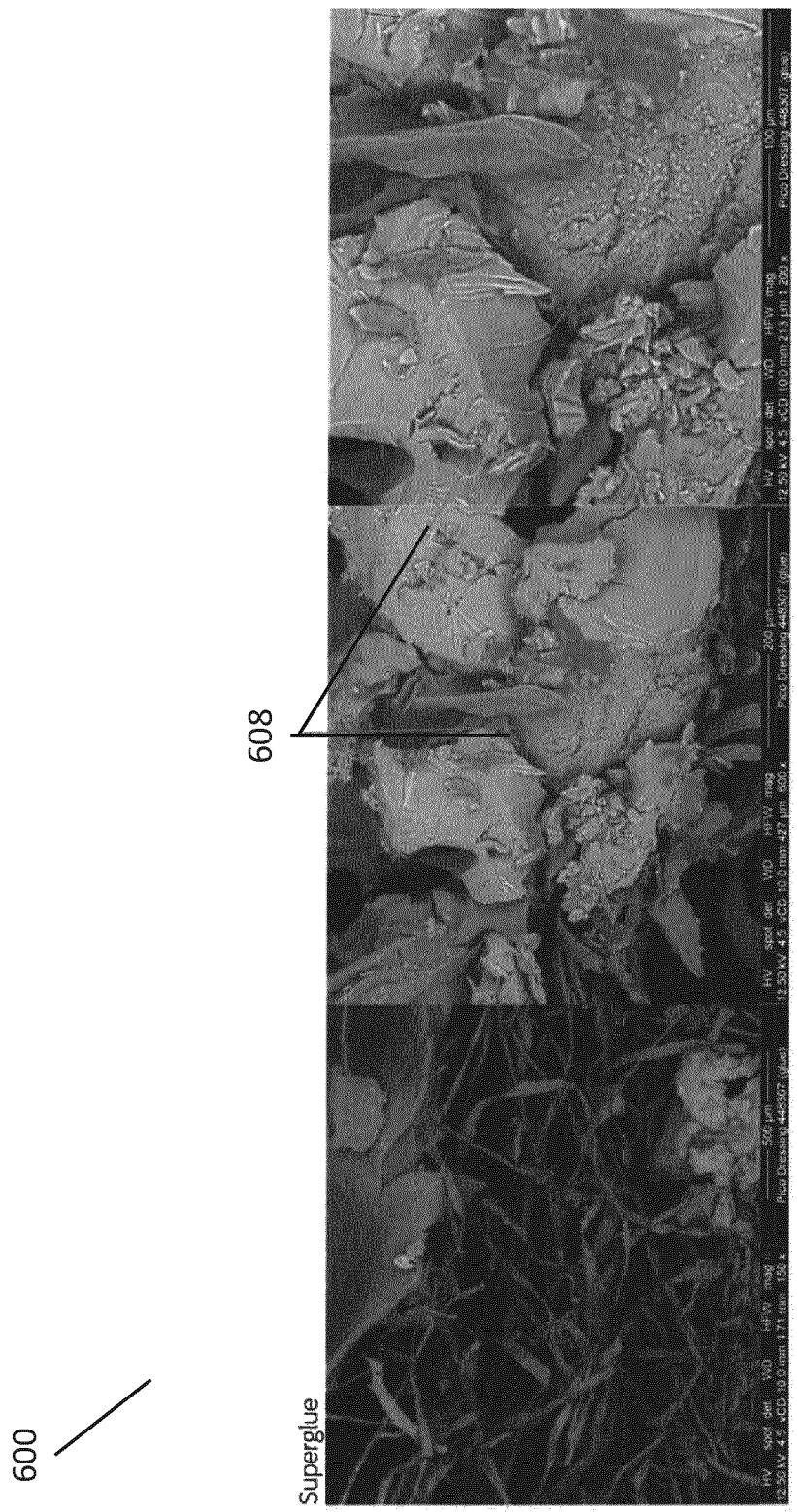
FIG. 7 shows multiple SEM micrographs of embodiments of wound dressings with glue on the backing layer.

FIG. 7 is a further series of SEM images of the wound dressing of FIG. 6. As in FIG. 6, glue has been applied to the backing layer of the dressing. Here, granular particulates 608 cover sections of super absorbent particles.

Figure 8:
FIG. 8 shows multiple SEM micrographs of embodiments of wound dressings without glue on the backing layer.

FIG. 8 is a series of SEM images of a wound dressing 700, similar to the dressings of FIGS. 6-7, however here no superglue has been applied and no granular particulates are observed.

Dressing Materials to Control Fluid Flow

As discussed with reference to FIG. 2C previously, a partition 1362 can be used between the absorbent area 1360 and the electronics area 1361 of a wound dressing containing the pump and electronics. The partition 1362 can separate the absorbent layer 1322 and lower air flow spacer layer 1311 from the electronic housing segment of the dressing in the electronic area. In some embodiments, materials can be incorporated into the dressing or to be used in place of or in addition to the partition 1362 to prevent wound fluid from entering the electronic housing section of the dressing. In some embodiments, the partition can be any material that completely or partially separates the absorbent area from the electronics area. In some embodiments, the dressing layers and/or electronic components can be coated with hydrophobic or hydrophilic coatings to provide the necessary separation of the absorbent area 1360 and electronics area 1361. In some embodiments, the dressing layers and/or electronic components can be made of hydrophobic or hydrophilic materials. For example, as shown in FIG. 2C, the non-porous dam 1362 can include a cyanoacrylate adhesive bead or a strip of silicone.

In some embodiments, the absorbent area and electronics area can be separated by using an epoxy material or similar material. The epoxy material can be used in a manner similar to the use of the glue as described above with reference to FIGS. 3-8. For example, a silicone type adhesive can be used to direct fluid flow within the dressing in a similar manner to the use of the glue described above. The silicone adhesive can be a flexible adhesive that can seal to the area where it is applied. The silicone adhesive is hydrophobic which allows the fluid within the dressing to be diverted around or away from the silicone. In other embodiments, the hydrophobic or hydrophilic materials and coatings of the dressing and electronic components can be utilized to control and direct the flow of fluid within the dressing.

In some embodiments, the wound dressing with incorporated pump and electronics does not include a dam or structure separating the electronics and absorbent area. The wound dressing can instead utilize hydrophobic or hydrophilic properties of the materials to control fluid flow and protect the electronics from the fluid within the dressing. In some embodiments, the wound dressing can include a lower spacer layer 1311 that extends from the absorbent area to the electronics area or a separate spacer layer between the electronics area and wound contact layer. Therefore, a lower spacer layer could be positioned between the absorbent layer and wound contact layer in the absorbent area and between the electronics and the wound contact layer in the electronics area. The lower spacer layer can be formed of, treated with, or coated with a hydrophilic agent as described above that directs the fluid through the spacer layer, into the absorbent layer, and away from the electronics.

In some embodiments, a portion of the absorbent layer can be formed of, treated with, or coated with a hydrophobic material. For example, the absorbent layer located in or directly adjacent to the electronics area can be formed of, treated with, or coated with a hydrophobic material to direct fluid away from the pump and/or electronics and prevent fluid from pooling around the pump and/or electronics. The portion of the absorbent layer that does not include a hydrophobic material may act as described with reference to FIGS. 2A-2C and prevent liquid collected in the wound dressing from flowing freely within the dressing. In some embodiments, the portion of the absorbent layer that does not include a hydrophobic material preferably acts so as to contain any liquid collected within that portion of the dressing. In some embodiments, all the dressing layers within the electronics area can be formed of, treated with, or coated with a hydrophilic material.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of certain embodiments herein, and may be defined by claims as presented herein or as presented in the future.

What is claimed is:

1. A wound dressing comprising:
   a wound contact layer configured to be positioned in contact with a wound;
   a first area over the wound contact layer comprising:
      a lower spacer layer; and
      an absorbent layer;
   a second area over the wound contact layer comprising a plurality of spacer layers and a negative pressure source and/or electronic components positioned within or between the plurality of spacer layers, wherein the first area is positioned adjacent to and horizontally offset from the second area and separated by a partition formed by an epoxy material applied to one or more layers of the first area and/or the second area;
   an upper spacer layer configured to cover the first area and the second area and to allow air to be communicated between the first area and second area around the partition; and
   a cover layer configured to cover and form a seal over the wound contact layer, the first area, and the second area.

2. The wound dressing of claim 1, wherein the epoxy material comprises a flexible hydrophobic material.

3. The wound dressing of claim 1, wherein the epoxy material comprises a silicone adhesive.

4. The wound dressing of claim 1, wherein the plurality of spacer layers in the second area comprise a first spacer layer beneath the negative pressure source and/or electronic components and a second spacer layer positioned above the negative pressure source and/or electronic components, wherein the second spacer layer comprises one or more cutouts or recesses configured to receive the negative pressure source and/or electronic components.

5. The wound dressing of claim 1, further comprising one or more user interface components configured to allow a user to operate the negative pressure source and/or electronic components.

6. A wound dressing comprising:
a wound contact layer configured to be positioned in contact with a wound;
a first area over the wound contact layer comprising:
a lower spacer layer;
an absorbent layer;
a second area over the wound contact layer comprising a plurality of layers and a negative pressure source and/or electronic components positioned within or between the plurality of layers,
wherein the first area is positioned adjacent to and horizontally offset from the second area; and
wherein at least one or more layers of the plurality of layers of the second area is at least partially coated with a hydrophobic material surrounding the negative pressure source and/or electronic components;
an upper spacer layer configured to cover the first area and the second area and to allow air to be communicated between the first area and second area; and
a cover layer configured to cover and form a seal over the wound contact layer, the first area, and the second area.

7. The wound dressing of claim 6, wherein the absorbent layer comprises a portion adjacent to the second area and wherein the portion adjacent to the second area comprises a hydrophobic material.

8. The wound dressing of claim 6, wherein the plurality of layers in the second area comprise a first spacer layer beneath the negative pressure source and/or electronic components and a second spacer layer positioned above the negative pressure source and/or electronic components, wherein the second spacer layer comprises one or more cutouts or recesses configured to receive the negative pressure source and/or electronic components.

9. The wound dressing of claim 6, wherein the plurality of layers in the second area comprise a first spacer layer beneath the negative pressure source and/or electronic components, wherein the first spacer layer and the lower spacer layer are one continuous layer positioned below the absorbent layer and the negative pressure source and/or electronic components and above the wound contact layer.

10. The wound dressing of claim 6, further comprising one or more user interface components configured to allow a user to operate the negative pressure source and/or electronic components.

* * * * *